United States Patent

Klinkmann et al.

[11] Patent Number: 4,929,784
[45] Date of Patent: May 29, 1990

[54] PROCESS FOR THE PREPARATION OF OPTIONALLY SUBSTITUTED BENZYL-BENZENES

[75] Inventors: Kurt Klinkmann, Nettersheim; Michael Herzhoff, Much; Gerhard Burmeister, Leverkusen, all of Fed. Rep. of Germany

[73] Assignee: Bayer Aktiengesellschaft, Leverkusen, Fed. Rep. of Germany

[21] Appl. No.: 419,994

[22] Filed: Oct. 11, 1989

[30] Foreign Application Priority Data

Oct. 28, 1988 [DE] Fed. Rep. of Germany ....... 3836780

[51] Int. Cl.$^5$ .............................................. C07C 2/02
[52] U.S. Cl. ..................... 585/422; 568/630; 568/648; 568/716; 568/763; 570/129; 570/184
[58] Field of Search ............... 585/422; 568/630, 716, 568/648, 763; 570/129, 184

[56] References Cited

U.S. PATENT DOCUMENTS

| | | | |
|---|---|---|---|
| 2,914,579 | 11/1959 | Erich | 585/422 |
| 4,251,675 | 2/1981 | Engel | 585/422 |
| 4,438,027 | 3/1984 | Mathais et al. | 570/184 |

FOREIGN PATENT DOCUMENTS

| | | | |
|---|---|---|---|
| 0638756 | 11/1936 | Fed. Rep. of Germany . | |
| 49-030345 | 3/1974 | Japan | 585/422 |

OTHER PUBLICATIONS

Benzylation of Aromatic Hydrocarbons in Presence of Activated Clay, Petrova et al., J. Gen. Chem. (USSR), vol. 20: pp. 2249–2253 (1950).

Primary Examiner—H. M. S. Sneed
Assistant Examiner—J. Saba
Attorney, Agent, or Firm—Sprung Horn Kramer & Woods

[57] ABSTRACT

Optionally substituted benzyl-benzenes can be prepared by reaction of a benzyl alcohol of the formula

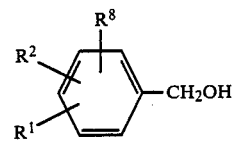

with a benzene of the formula

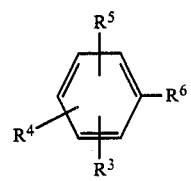

in which
$R^1$, $R^2$, $R^3$, $R^4$ and $R^5$ independently of one another denote hydrogen, $C_1$–$C_4$-alkyl, $C_1$–$C_4$-alkoxy, fluorine or chlorine, where $R^1$, $R^2$, $R^3$ and $R^4$ independently of one another may also represent hydroxyl and $R^5$ may additionally be $C_5$–$C_8$-alkyl,
$R^6$ represents hydrogen or one of the groups

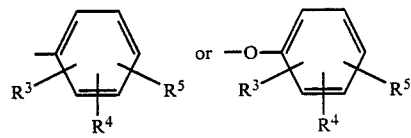

$R^8$ denotes hydrogen or hydroxymethyl,
in a ratio of 1 mole of benzene to 0.8–5 moles of benzyl alcohol in the presence of an amount of activated bleaching earth of 0.05–5% by weight, relative to the amount of benzyl alcohol, at a temperature between 90° C. and 140° C. in the presence of a diluent.

11 Claims, No Drawings

PROCESS FOR THE PREPARATION OF OPTIONALLY SUBSTITUTED BENZYL-BENZENES

BACKGROUND OF THE INVENTION

1. Field of the invention

The invention relates to a process for the preparation of optionally substituted benzyl-benzenes by reaction of optionally substituted benzyl alcohols or the dibenzyl ethers produced from them with optionally substituted benzenes in the presence of activated bleaching earth at elevated temperature.

Optionally substituted benzyl-benzenes are, for example, diphenylmethane, benzyl-toluene, dibenzyl-benzenes, dibenzyl-toluenes, benzyl-biphenyl etc. The compounds mentioned are known to the person skilled in the art.

2. Description of the related art

Benzyl-benzenes of the type mentioned can be prepared by known methods by reaction of suitable aromatics with formaldehyde. Now, recently, apart from the toxic properties of many aromatics used, the maximum allowable concentration (MAC) for formaldehyde has been very greatly reduced. This means high outlays on work safety and on the effective suppression of any emission into the air or the waste water. By means of this, formaldehyde chemistry of this type is made prohibitively expensive.

In other, likewise known processes, suitable aromatics can be benzylated using benzyl chloride, for example in the presence of Friedel-Crafts catalysts. However, both the catalysts used in this case and a residual chlorine content or chlorine eliminated from the benzyl chloride produce large corrosion problems for the apparatus used in such processes. The resultant benzylated products retain a residual chlorine content which makes them thermally unstable and therefore makes use, for example, as a heat transfer oil problematical.

In addition, benzal chloride is always formed at the same time in the preparation of benzyl chloride by side chain chlorination of toluene. However, benzyl chloride and benzal chloride can only be separated by distillation in expensive nickel columns on account of the corrosion problems.

In principle, it should be possible to replace the benzyl chloride by benzyl alcohol for the purposes of benzylation. Such a replacement could have substantial advantages: first of all, benzyl alcohol would not produce the feared chloride ion corrosion in such a process; chloride ion corrosion occurring in the preparation of benzyl alcohol from benzyl chloride would in any case remain in the preparation process from benzyl alcohol or benzyl chloride, where it must always be overcome if it is intended to prepare benzyl chloride or benzyl alcohol for other purposes than those of the present invention. Secondly, the separation of the benzaldehyde always additionally resulting (from inevitable benzal chloride) in the preparation of benzyl alcohol from benzyl chloride might be possible in a normal steel distillation column (instead of the above-mentioned nickel column). Therefore attempts have already been made to carry out the benzylation with benzyl alcohol in the presence of sulphuric acid or phosphoric acid. However, such attempts produced large amounts of resinous reaction products in addition to the new corrosion by the strong acids mentioned.

It has also already been attempted to replace the strong mineral acids mentioned by bleaching earth in the benzylation with benzyl alcohol. Attempts of this type have been published at long intervals, without hitherto becoming economically useful.

Thus, DE-PS 638,756 discloses the reaction of 2 parts of benzyl alcohol with 4 parts of benzene (molar ratio 1:2.77) at 230° C. in an autoclave. 50% by weight of Tonsil, relative to the benzyl alcohol, are employed for this. Diphenylmethane is prepared in a yield of about 40% of the theoretical yield and dibenzyl-benzenes in a yield of about 25%, all yields relating to benzyl alcohol.

Benzylation of some aromatics with benzyl alcohol in the presence of askanite is known from J. General Chemistry of the USSR (English translation of Z. obsz. Zhim.) 20 (1950), 2249 (page 2168 in the original). This procedure is carried out at 90° C. and at 10% by weight of askanite, relative to the benzyl alcohol. If 200 g of benzyl alcohol and 200 g of benzene (molar ratio 1:1.38) are used, about 16% of diphenylmethane and 4.6% of dibenzyl-benzene, all relative to benzyl alcohol, are obtained; the non-distillable residue is larger than the total amount of diphenylmethane and dibenzyl-benzene. In the benzylation of toluene under the same conditions 10.8% of dibenzyl-toluene, both relative to benzyl alcohol, are obtained.

Reworking of both literature sources gave, in addition to the low yields, dark brown reaction products which in this form can be put to no further use.

SUMMARY OF THE INVENTION

It has now surprisingly been found that substantially larger amounts of reaction products are obtained if the reaction is carried out using substantially smaller amounts of activated bleaching earth in the temperature range mentioned further below and the reaction components are kept sufficiently dilute, although this has to be regarded as technically retrograde on account of the lower space yield. The reaction is then so easy to control that with regard to the distribution, of higher and lower molecular weights, the reaction products can be very easily differentiated.

The invention accordingly relates to a process for the preparation of benzyl-benzenes of the formula

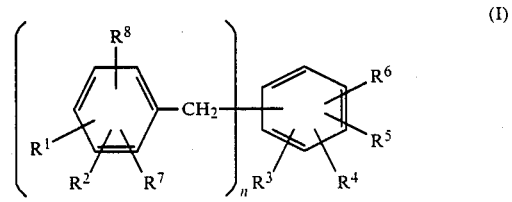

in which $R^1$, $R^2$, $R^3$, $R^4$ and $R^5$ independently of one another denote hydrogen, $C_1$–$C_4$–alkyl, $C_1$–$C_4$–alkoxy, fluorine or chlorine, where $R^1$, $R^2$, $R^3$ and $R^4$ independently of one another may also represent hydroxyl and $R^5$ may additionally be $C_5$–$C_8$–alkyl, $R^6$ represents hydrogen or one of the groups

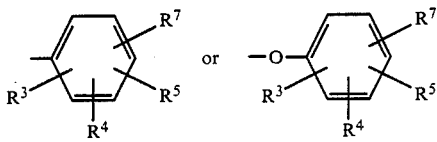

R$^7$ represents hydrogen or the group

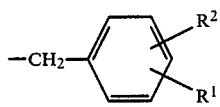

n represents the number 1 or 2 and may also represent the number 3 in the case in which one of the radicals R$^3$, R$^4$, R$^5$ or R$^6$ denotes hydrogen,
which is characterized in that a benzene of the formula

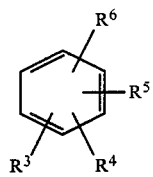 (II)

is reacted with a benzyl alcohol of the formula

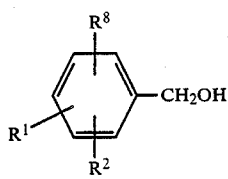 (III)

where
R$^1$ to R$^5$ have the abovementioned meaning,
R$^6$ represents hydrogen or one of the groups

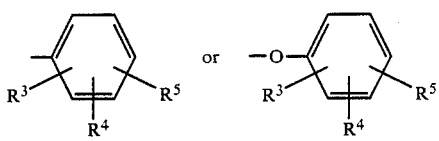

and
R$^8$ denotes hydrogen or hydroxymethyl,
in a ratio of 1 mole of benzene to 0.5–5 moles of benzyl alcohol in the presence of an amount of activated bleaching earth of 0.05–5% by weight, relative to the amount of benzyl alcohol, at a temperature between 90° C. and 140° C. in the presence of a diluent.

DETAILED DESCRIPTION OF THE INVENTION

C$_1$–C$_8$-Alkyl and C$_1$–C$_4$-alkoxy are, for example, methyl, ethyl, propyl, i-propyl, butyl, i-butyl, straight-chain or branched amyl, hexyl, heptyl or octyl, methoxy, ethoxy, propoxy, i-propoxy, butoxy or i-butoxy. C$_1$–C$_4$-Alkyl is preferred, methyl and ethyl are particularly preferred; methoxy and ethoxy are preferred alkoxy.

Benzyl alcohols which may be preferably employed in the process according to the invention are those of the formula

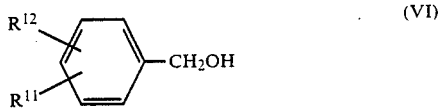 (VI)

in which
R$^{11}$ and R$^{12}$ independently of one another denote hydrogen, methyl, ethyl, fluorine or chlorine and R$^{11}$ may additionally represent hydroxymethyl.

Particularly preferred benzyl alcohols for the process according to the invention are those of the formula

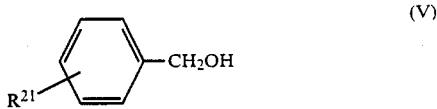 (V)

in which
R$^{21}$ denotes hydrogen, methyl or ethyl.

In a very particularly preferred manner, the unsubstituted benzyl alcohol is employed.

Preferred benzene compounds for the process according to the invention are those of the formula

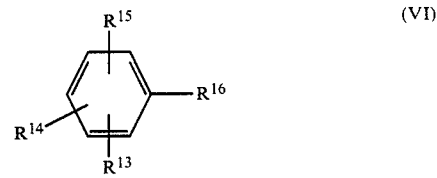 (VI)

in which
R$^{13}$, R$^{14}$ and R$^{15}$ independently of one another denote hydrogen, C$_1$–C$_4$-alkyl, fluorine or chlorine and R$^{13}$ may furthermore represent hydroxyl and
R$^{16}$ represents hydrogen or one of the groups

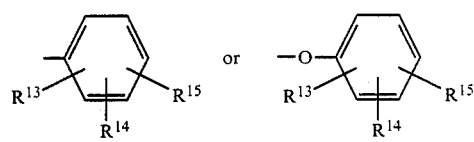

Particularly preferred benzene compounds are those of the formula

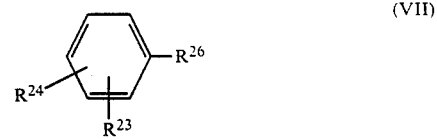 (VII)

in which
R$^{23}$ and R$^{24}$ independently of one another denote hydrogen, methyl, ethyl, fluorine or chlorine and R$^{23}$ may additionally represent hydroxyl and
R$^{26}$ represents hydrogen, methyl or one of the groups

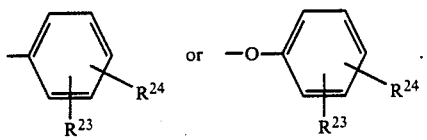

Very particularly preferred benzene compounds for the process according to the invention are those of the formula

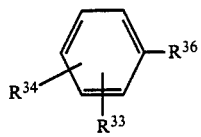

(VIII)

in which
$R^{33}$ and $R^{34}$ independently of one another denote hydrogen, methyl, ethyl or chlorine and $R^{33}$ may additionally represent hydroxyl and
$R^{36}$ represents hydrogen, methyl or phenyl substituted by $R^{33}$ and $R^{34}$.

Other preferred benzenes of the formula (II) and (VI) are those in which one, preferably two, particularly preferably three, of the substituents mentioned represent hydrogen. In an analogous manner, preferred benzenes are furthermore those of the formula (VII) and (III) in which one, preferably two, of the substituents mentioned denotes hydrogen.

Important benzene compounds for the process according to the invention are, for example: benzene, toluene, xylene, mesitylene, ethylbenzene, diethylbenzene, propylbenzene, isopropylbenzene, diisopropylbenzene, phenol, cresols, diphenyl and diphenyl ether.

Activated bleaching earth which may be employed according to the invention is taken to mean clays which have been subjected to acid treatment. Clays for this purpose are predominantly minerals of the montmorillonite group which includes bentonites, nontronites, baydellites and hectorites. Suitable clays for the preparation of activated bleaching earths are found as natural minerals, but may also be synthesized artificially. Activated bleaching earths are marketed under many commercial names, for example as Floridin, Tonsil, Terrana, Clarit, Filtrol, Nordal, Rumsil and others. Such activated bleaching earths are known to the person skilled in the art and are dealt with, for example, in Ullmanns Encyclopädie der technischen Chemie (Ullmann's Encyclopaedia of Industrial Chemistry), 3rd edition, volume 4 (1953) p. 541 ff.

The activated bleaching earth is employed according to the invention in an amount of 0.05-5% by weight, preferably 0.07-2% by weight, particularly preferably 0.1-1% by weight, relative to the benzyl alcohol dibenzyl ether produced from this.

The process according to the invention is carried out at a temperature between 90° and 140° C., preferably at 95°-130° C., particularly preferably at 100°-120° C. In a very particularly preferred manner, the process is carried out at the boiling temperature of the reaction mixture. In some cases, this is the boiling point of the benzene compound to be employed. If the boiling point of the benzene compound does not fall in the range of the reaction temperature indicated, the boiling point of the benzene compound can be attained in a manner known to the person skilled in the art by slight elevation of pressure (for example when using benzene) or by corresponding reduction of pressure (for example when using xylene and other higher-boiling benzene compounds). The adjustment of boiling conditions in the context of the reaction temperature mentioned may also be attained, however, by addition of inert, i.e. not engaging in the course of the reaction, solvents or diluents. Such solvents have a boiling point within the range of the reaction temperature indicated or only a little under this. Such inert solvents are, for example, cyclohexane, methyl-cyclohexane, dimethyl-cyclohexane, iso-octane and other (cyclo)aliphatic hydrocarbons boiling in the range of the reaction temperature.

In the case of cyclohexane having a boiling point of about 81° C., a bottom temperature is set in the reaction mixture which, under the influence of all reaction participants, is higher than the boiling temperature of the cyclohexane, in fact even higher the less cyclohexane is added to the reaction mixture. The desired reaction temperature can thus be adjusted in a desired manner by means of the amount of inert solvent (for example cyclohexane) added.

Water of reaction is formed in the process according to the invention; this is 1 mole of water per mole of benzyl alcohol reacted. The water of reaction can in principle remain in the reaction mixture and only be separated off on working up. In a preferred manner, however, the water of reaction is already removed and purged from the reaction mixture during the condensation by distillation. In this case, the fact is used in an advantageous manner that many benzenes and inert solvents form an azeotrope with water, which is separated again after the condensation outside the reaction mixture in a water separator into the organic compound and water. The benzene or the solvent or a mixture of both is again fed back into the reaction mixture, while the purged water is used as a measure of the progress of the reaction.

The benzyl-benzenes of the formula (I) which can be prepared in the process according to the invention have the structure

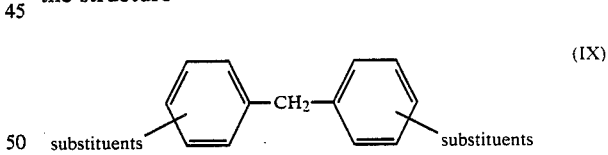

(IX)

in which the radicals mentioned above in detail are inclusively designated as "substituents" (S).

The benzene can also be benzylated twice so that the following structure results:

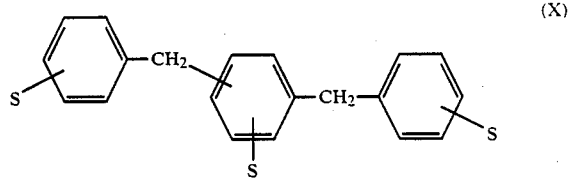

(X)

If the reaction starts from a phenyl-benzene (=biphenyl) or a phenoxy-benzene (=diphenyl ether) ($R^8$, $R^{18}$, $R^{28}$ or $R^{38}$), the following structures result:

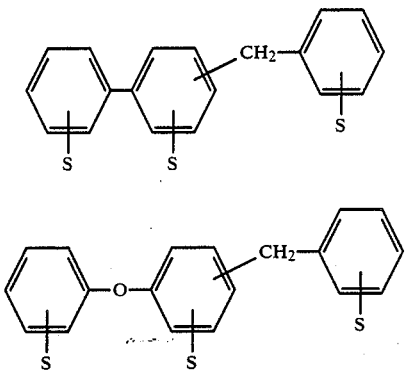

and also the types benzylated twice on an aromatic ring, the types each benzylated singly on an aromatic ring and structures which are derived from tribenzyl-biphenyl or tribenzyl-diphenyl ether. Finally, an added benzyl group may in turn be benzylated.

In order to achieve the different degrees of benzylation, 0.5–5 moles of benzyl alcohol are employed per mole of benzene. Using 0.5–1.1 moles of benzyl alcohol, single benzylation is essentially achieved. Using 1.5–2.2 moles of benzyl alcohol, double benzylation is essentially achieved. Using still larger amounts, further increased degrees of benzylation are achieved in an immediately apparent manner. With the setting of the degree of benzylation 1, doubly benzylated products occur in secondary amounts. With higher degrees of benzylation, the spectrum of different highly benzylated products is wider. If mixtures are desired, molar numbers differing more greatly from integers may also be used, for example 1.1–1.5, 1.3–1.9 or 2.2–2.7 moles of benzyl alcohol per mole of benzene or yet other (even higher) molar ranges within the entire range mentioned.

With higher benzylation, if it is also wished to keep the spectrum of the different highly benzylated benzenes narrow, it is in addition possible to isolate the benzene benzylated singly in the manner described first and to subject it again to monobenzylation.

The products of the process according to the invention can be separated into individual components by distillation. In this connection, distillation is advantageously carried out under reduced pressure because of the very high boiling points. The 2-ring compounds and the 3-ring compounds can be isolated in this way without a relatively large outlay on distillation. The isolation of more highly condensed substances becomes increasingly more difficult, and thus they are advantageously used further as a mixture. The 2-ring compounds and 3-ring compounds are useful intermediates which are accessible to further reaction by known methods of aromatic chemistry. Moreover, all substances which can be prepared according to the invention are characterized by outstanding thermal stability so that they are suitable as heat transfer media. A still further outstanding aptitude is given by the outstanding insulating properties as electrical insulating fluids, for example for substations, capacitors and transformers. On account of the isolability by distillation and specific preparation of the 2-ring and 3-ring compounds, these compounds can already be employed as crude products both individually and as mixtures for use as heat transfer agents or as electrical insulating fluid. With the aid of the process according to the invention, a large variety of different viscosities and graduations of other properties are possible. The 4-ring compounds and still higher compounds are in general left as a mixture and find application as useful resinous materials, for example for embedding electrical devices, as plasticizers for polymers, as tackifying resins in the rubber industry etc.

For all uses mentioned, it is of prime importance that the products of the process according to the invention are absolutely free of chlorine and thus cause no corrosion or self-decomposition. This is important in comparison, for example, to benzyl-benzenes which are prepared by benzylation using benzyl chloride; typically, a tarry residue remains in the benzyl chloride condensation after distilling off the lower reaction products, whereas the resinous residue of the process according to the invention, the uses of which have just been mentioned, is honey-yellow. The process according to the invention is carried out using a surprisingly low amount of activated bleaching earth. The process according to the invention furthermore has no waste water and waste air pollution like the prior art processes; in particular there is no formaldehyde emission.

It is an important characteristic of the process according to the invention that it is carried out in the presence of a diluent, which has already been mentioned further above for adjusting the reaction temperature under boiling conditions. These diluents must not be benzylatable under the process conditions. Among these, cyclohexane is very particularly important.

The diluent is employed in an amount from 40–2000% by weight, relative to the benzene to be reacted. On economical grounds, the upper part of the range mentioned is only used if the degree of benzylation is intended to be very accurately adjusted; otherwise 40–400% by weight suffice, in many cases even 40–200% by weight, relative to the benzene.

In the case in which the degree of benzylation 1 is desired, it is possible to employ the benzene to be benzylated in excess as a diluent instead of a non-benzylated diluent. Above all, this is important with the low-boiling starting benzenes, such as benzene, toluene, xylene, fluorobenzene and chlorobenzene. In this case, degrees of dilution in the upper part of the range mentioned are used.

The process according to the invention can be carried out in a variety of ways. Thus, for example, it is possible in the manner already indicated to separate off the resultant water of reaction only on working up the reaction mixture or, in a preferred manner, even while carrying out the reaction. Furthermore, it is possible to initially introduce all starting materials including the activated bleaching earth and the diluent together and to heat to the desired reaction temperature. In addition, it is possible to initially introduce the benzene, the diluent and the activated bleaching earth and to heat to the reaction temperature and only then to add the benzyl alcohol. Such an addition is carried out in a preferred manner according to the production of water, for which purpose during the reaction, the water of reaction is already separated off from the reaction mixture in the manner described in such a preferred case.

In addition, it is possible to initially introduce solvent, benzyl alcohol and bleaching earth and to initiate self-condensation of the benzyl alcohol with purging of the water of reaction. Hereby, both dibenzyl ether and also mono- or polybenzylated benzyl ether are formed. After addition of the benzene compound, the self-condensation is discontinued and the benzyl groups are transferred to the benzene compound.

This variant shows that, instead of the benzyl alcohol, basically its accompanying dibenzyl ether can be employed. In this connection, a part of the molar amount of water reaction liberated per mole of benzyl alcohol is already liberated in the formation of ether or ongoing benzylation of this ether. In connection with the following of the benzylation of the benzene by the elimination of water of reaction, this previously already eliminated water of reaction must be taken into account. Of course, the total benzyl alcohol consumed for the formation of the dibenzyl ether or that for the benzylation of such a dibenzyl ether is regarded as the molar amount of benzyl alcohol to be employed. This formation of the benzyl ether and its breaking up is particularly advantageous with poorly active (for example with halogenated) benzenes.

In another advantageous process variant, the reaction according to the invention can be increased in the presence of a diluent: thus is it not only, possible to add the benzyl alcohol uniformly metered (on the laboratory scale, for example, dropwise) to the surface of the diluted benzene or better through a dip tube into the solution and to distribute it rapidly and uniformly therein by intensive stirring, but a diluent may also be back from the water separator and originally employed for the dilution of benzene or a carrier gas, for example air or $N_2$, with which the benzyl alcohol is also diluted in addition to the initially introduced benzene. In particular, such a carrier gas is advantageous since the benzyl alcohol is passed by it into the diluted benzene solution through a jet of a dip tube in the vicinity of the stirrer.

In order to work up the reaction product, the diluent is distilled off before or after the separation of the bleaching earth and the benzylated benzene is fractionated or used as the resulting mixture. In the preparation of more highly benzylated and thus more highly viscous reaction products, the case can occur in which the solvent power of the diluent is insufficient for trouble-free working up, since the diluent must not be benzylatable and is therefore aliphatic. It is of help here if, after the consumption of the total benzyl alcohol employed, an aromatic auxiliary solvent, for example benzene or toluene, is added before or during the distilling off of the diluent, and then the process is further carried out as described.

EXAMPLES

Example 1 (benzyltoluene)

3.170 ml of toluene and 10.5 g of bleaching earth (Tonsil K 10 from Südchemie AG) were heated to boiling in a stirring vessel with a distillation passage, condenser and water separator. 216 g of benzyl alcohol were then passed in through a jet in the course of about 2 hours, i.e. benzyl alcohol was added dropwise under a flow of nitrogen (100 l/h) via an immersed thin tube and in this way was rapidly and uniformly distributed and made to react.

Rapid metering in of the benzyl alcohol was possible and was kept equivalent to the water produced.

| Time (h.min.) | Bottom temp. °C. | Benzyl alcohol (ml) | Water distilled off (ml) |
|---|---|---|---|
| 0 | 110 | 0 | |
| 0.30 | 110 | 60 | 9 |
| 1.00 | 111 | 110 | 20 |
| 1.30 | 112 | 170 | 29 |
| 1.50 | 112 | 210 | 34 |

About 1-2 g of water were lost with the stream of nitrogen.

A subsequent reaction time of about 30 minutes sufficed to complete condensation. The unreacted toluene was then distilled off through a short column and thus at the same time purified for further use. The residual toluene was removed from the crude condensate and likewise recovered in a rotary evaporator at 20-50 mm Hg and a bottom temperature of a maximum of 100° C. Finally, the bleaching earth was removed by filtration.

On an average of several experiments, 345 g=95% of the theoretical yield (relative to benzyl alcohol) of benzyltoluene was obtained. The product contained only small percentages of dibenzyltoluene (6-8% in the course of several experiments); it could be employed immediately in the form produced as a water-clear liquid, for example as an electrical insulating fluid. Chlorine was not detectable.

Example 2 (polybenzyldiphenyl)

In the synthesis of more highly condensed products, the introduction of the benzyl alcohol was carried out at an always constant condensation temperature which was favourably 108°-110° C. The introduction of the benzyl alcohol was carried out in a similar manner to that in Example 1. The necessary constant condensation temperature of 108°-110° C. was achieved by addition of cyclohexane as an inert water entrainer for the reaction. For this, just sufficient cyclohexane was added to the initially introduced diphenyl so that the cyclohexane boiled under reflux from the cyclohexane-diphenyl mixture at a bottom temperature of 108°-110° C. The bottom temperature and thus the condensation temperature was kept constant at 108°-110° C. by further uniform metering in of cyclohexane during the entire condensation process.

Viscous reaction mixtures were obtained after completion of the condensation. The separation of the bleaching earths from these was not directly possible, but was carried out by centrifuging after diluting with additional cyclohexane in the ratio 1:1.

In a further working up variant, xylene or toluene was added after complete conversion of the benzyl alcohol. The cyclohexane used in the condensation was distilled off with continuous addition of xylene or toluene and recovered for use again. If the condensate was dissolved in a sufficient amount of xylene or toluene, it was possible to remove the bleaching earth from the cyclohexane-free solution by centrifugation. The solvent (xylene or toluene) was removed by distillation and recovered from the final product now freed from bleaching earth. The solvent-free condensation product remained as a residue.

In detail, the process was carried out as follows:

300 ml of cyclohexane were added to 3 mol=462 g of diphenyl and the bottom temperature at reflux was adjusted to 108°-110 ° C. 4 g of bleaching earth were then added and 7.5 mol=810 g of benzyl alcohol were subsequently blown in via a dip tube using nitrogen (100 1/h).

| Time (h.min.) | Bottom temp. °C. | Benzyl alcohol (ml) | Water distilled off (ml) | Cyclohexane added (ml) |
|---|---|---|---|---|
| 0 | 108 | 0 | 0 | |
| 0.20 | 110 | 100 | 10 | |
| 0.50 | 110 | 200 | 27 | 100 |
| 1.20 | 110 | 300 | 43 | |
| 1.40 | 110 | 400 | 58 | 200 |
| 2.10 | 110 | 500 | 75 | |
| 2.40 | 110 | 600 | 91 | 300 |
| 3.15 | 110 | 700 | 108 | |
| 3.45 | 110 | 800 | 115 | 400 |
| 4.45 | 110 | 810 | 125* | |
| | | | | total 400 |

*135 g of H₂O were to be expected theoretically. Water was lost through the flow of N₂.

The cyclohexane was distilled off in a rotary evaporator. 1.156 g of crude condensate containing bleaching earth and minimum cyclohexane residual moisture were obtained (theoretical 1.133 g).

The crude condensate was diluted with toluene (1:1) and centrifuged. The toluene was then distilled off in a rotary evaporator.

Example 3 (tribenzyltoluene)

The process was carried out in detail as follows according to the directions for Example 2:

300 ml of cyclohexane were added to 600 g of benzyl toluene and the bottom temperature was adjusted at reflux to 110° C. 4 g of Tonsil K 10 were then added and 800 g of benzyl alcohol were subsequently blown in via a dip tube using nitrogen (100 1/h).

| Time (h.min.) | Bottom temp (°C.) | Benzyl alcohol (ml) | H₂O produced (ml) | Cyclohexane added (ml) |
|---|---|---|---|---|
| 0 | 107 | 0 | 0 | |
| 0.30 | 110 | 100 | 15 | |
| 1.00 | 110 | 200 | 28 | 100 |
| 1.30 | 110 | 300 | 45 | |
| 2.00 | 110 | 400 | 58 | 200 |
| 2.30 | 110 | 500 | 75 | |
| 3.00 | 110 | 600 | 90 | 300 |
| 3.35 | 110 | 700 | 108 | |
| 4.10 | 110 | 800 | 122 | 400 |
| 4.40 | 110 | — | 122* | 500 |

*133 g of H₂O were to be expected theoretically. Water was lost through the flow of N₂.

1.5 l of toluene were added to the reaction mixture and the mixture was then centrifuged.

The crude condensate was obtained after distilling off the solvent.

Example 4

460 g of fresh toluene and 1719 g of recycled toluene were heated to boiling together with 2 g of Tonsil K 10 in a reactor with a stirrer and water separator. 650 g of benzyl alcohol were added dropwise to the boiling reaction mixture according to the production of water. The water was distilled off as the azeotrope with toluene and separated from the toluene in a water separator. The toluene was added to the reaction mixture again. Altogether, 108 g of water were produced. After completion of the reaction (detectable by discontinuation of the production of water), 3 g of calcium oxide were added to the reaction mixture and it was stirred. The mixture was then filtered and the toluene was distilled off from the filtrate (recovery of 1719 g of toluene). A crude yield of 937 g was obtained, which was subjected to a vacuum distillation. In this way, a first fraction consisting of benzyl-toluene was obtained in an amount of 687 g and a second fraction consisting of dibenzyltoluene in an amount of 172 g. The fractions 1 and 2 in a total amount of 859 g represent 91.6% of the crude yield. Vacuum distillation furthermore gave 67 g=7.1% of the crude yield, of honey-yellow resin. The rest was handling losses.

What is claimed is:

1. A process for the preparation of benzyl-benzenes of the formula

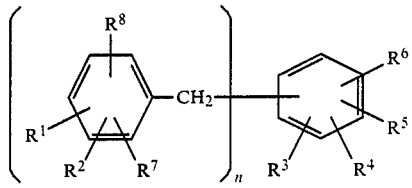

in which $R^1$, $R^2$, $R^3$, $R^4$ and $R^5$ independently of one another denote hydrogen, $C_1$-$C_4$-alkyl, $C_1$-$C_4$-alkoxy, fluorine or chlorine, where $R^1$, $R^2$, $R^3$ and $R^4$ independently of one another may also represent hydroxyl and $R^5$ may additionally be $C_5$-$C_8$-alkyl, $R^6$ represents hydrogen or one of the groups

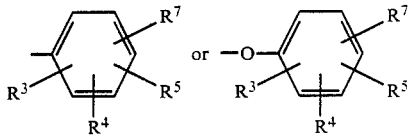

$R^7$ represents hydrogen or the group

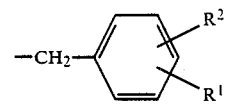

n represents the number 1 or 2 and may also represent the number 3 in the case in which one of the radicals $R^3$, $R^4$, $R^5$ or $R^6$ denotes hydrogen, wherein a benzene of the formula

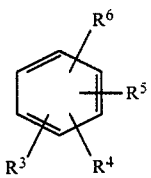

is reacted with a benzyl alcohol of the formula

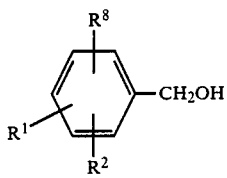

where
R$^1$ to R$^5$ have the abovementioned meaning,
R$^6$ represents hydrogen or one of the groups

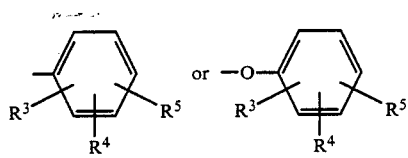

and
R$^8$ denotes hydrogen or hydroxymethyl,
in a ratio of 1 mole of benzene to 0.5–5 moles of benzyl alcohol in the presence of an amount of activated bleaching earth of 0.05–5% by weight, relative to the amount of benzyl alcohol, at a temperature between 90° C. and 140° C. in the presence of a diluent.

2. The process of claim 1, wherein a benzyl alcohol of the formula

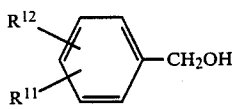

is employed in which
R$^{11}$ and R$^{12}$ independently of one another denote hydrogen, methyl, ethyl, fluorine or chlorine and R$^{11}$ may additionally represent hydroxymethyl.

3. The process of claim 2, wherein a benzyl alcohol of the formula

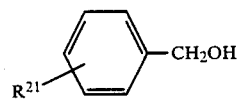

is employed in which
R$^{21}$ denotes hydrogen, methyl or ethyl.

4. The process of claim 1, wherein a benzene of the formula

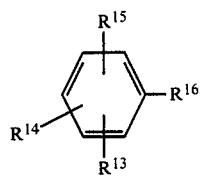

is employed in which

R$^{13}$, R$^{14}$ and R$^{15}$ independently of one another denote hydrogen, C$_1$–C$_4$-alkyl, fluorine or chlorine and R$^{13}$ may furthermore represent hydroxyl and
R$^{16}$ represents hydrogen or one of the groups

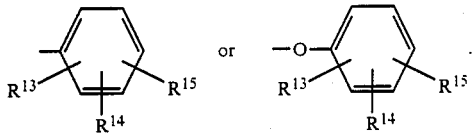

5. The process of claim 4, wherein a benzene of the formula

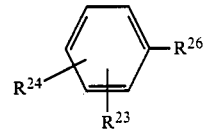

is employed in which
R$^{23}$ and R$^{24}$ independently of one another denote hydrogen, methyl, ethyl, fluorine or chlorine and R$^{23}$ may additionally represent hydroxyl and
R$^{26}$ represents hydrogen, methyl or one of the groups

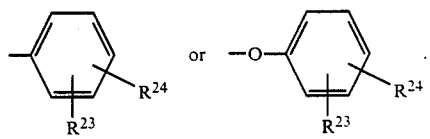

6. The process of claim 1, wherein a benzene of the formula

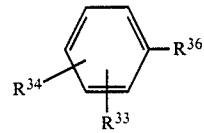

is employed in which
R$^{33}$ and R$^{34}$ independently of one another denote hydrogen, methyl, ethyl or chlorine and R$^{33}$ may additionally represent hydroxyl and
R$^{36}$ represents hydrogen, methyl or phenyl substituted by R$^{33}$ and R$^{34}$.

7. The process of claim 1, wherein the activated bleaching earth is employed in an amount of 0.07–2X by weight, relative to the benzyl alcohol.

8. The process of claim 7, wherein the activated bleaching earth is employed in an amount of 0.1–1% by weight, relative to the benzyl alcohol.

9. The process of claim 1, where the diluents are cyclohexane, methyl-cyclohexane or dimethyl-cyclohexane, employed in an amount of 40–2000% by weight, relative to the benzene to be benzylated.

10. The process of claim 1, wherein the benzyl alcohol is employed in a form diluted by the diluent or by a carrier gas.

11. The process of claim 10, wherein the benzyl alcohol is passed into the diluted benzene via a dip tube with the aid of an air or N$_2$ stream through a jet.

* * * * *

UNITED STATES PATENT AND TRADEMARK OFFICE
CERTIFICATE OF CORRECTION

PATENT NO. : 4,929,784

DATED : May 29, 1990

INVENTOR(S) : Klinkmann et al.

It is certified that error appears in the above-identified patent and that said Letters Patent is hereby corrected as shown below:

Col. 12, claim 1 line 50   After formula insert -- and --

Col. 14, claim 7 line 52   After " 0.07-2 " delete " X " and substitute -- % --

Signed and Sealed this

Fourth Day of February, 1992

Attest:

HARRY F. MANBECK, JR.

Attesting Officer

Commissioner of Patents and Trademarks